United States Patent [19]

Freitag et al.

[11] 4,393,009
[45] Jul. 12, 1983

[54] PROCESS FOR THE PREPARATION OF AROMATIC DICARBOXYLIC ACID DICHLORIDES

[75] Inventors: Dieter Freitag; Ludwig Bottenbruch; Claus Wulff, all of Krefeld, Fed. Rep. of Germany

[73] Assignee: Bayer Aktiengesellschaft, Leverkusen, Fed. Rep. of Germany

[21] Appl. No.: 280,898

[22] Filed: Jul. 6, 1981

[30] Foreign Application Priority Data

Jul. 3, 1979 [DE] Fed. Rep. of Germany ...... 2926736

[51] Int. Cl.$^3$ .............................................. C07C 51/60
[52] U.S. Cl. ................................................. 260/544 K
[58] Field of Search ................................... 560/544 K

[56] References Cited

U.S. PATENT DOCUMENTS

| | | | |
|---|---|---|---|
| 2,657,233 | 10/1953 | Carnahan | 260/544 K |
| 2,848,491 | 8/1958 | MacKenzie et al. | 260/544 K |
| 3,318,950 | 5/1967 | Christoph et al. | 260/544 |
| 3,547,960 | 12/1970 | Hauser | 260/544 K |
| 3,857,841 | 12/1974 | Keil | 260/544 K |
| 4,129,594 | 5/1978 | Baker et al. | 260/544 |

FOREIGN PATENT DOCUMENTS

| | | | |
|---|---|---|---|
| 401643 | 2/1932 | United Kingdom . | |
| 540096 | 10/1941 | United Kingdom | 260/408 |
| 1159266 | 7/1969 | United Kingdom | 260/544 K |
| 1434400 | 5/1976 | United Kingdom . | |

OTHER PUBLICATIONS

Csuros, Zoltan et al., *Chemical Abstracts*, vol. 76, (1972), #112,720k.

*Primary Examiner*—Anton H. Sutto
*Assistant Examiner*—L. Hendriksen
*Attorney, Agent, or Firm*—Connolly and Hutz

[57] ABSTRACT

Process for the preparation of pure aromatic dicarboxylic acid dichlorides which comprises reacting an aromatic dicarboxylic acid or an aromatic dicarboxylic acid mixture with phosgen in one stage and in the presence of an N—$C_1$—$C_6$-alkyl-pyrrolidine, -piperidine or -morpholine as a catalyst and optionally in a solvent or diluent.

2 Claims, No Drawings

PROCESS FOR THE PREPARATION OF AROMATIC DICARBOXYLIC ACID DICHLORIDES

This invention relates to a one-shot process for the preparation of high purity aromatic dicarboxylic acid dichlorides which are capable of polycondensation.

The preparation of aliphatic and aromatic acid chlorides by the reaction of a carboxylic acid with phosgene has been described in U.S. Pat. Nos. 3,184,506; 3,544,626; 3,544,627 and 3,547,960 and in German Offenlegungsschrift No. 2,400,007. The reaction products of these processes are dark coloured carboxylic acid chlorides obtained having a degree of purity of from 96 to 99%. Aromatic dicarboxylic acid dichlorides having such a low degree of purity cannot be used directly in the diphasic interface polycondensation process for the preparation of high molecular weight polycondensates, such as aromatic polyamides or aromatic polyesters. The unreacted or only semi-reacted dicarboxylic acids present in these reaction products interferes with polycondensation, causes chain-breaking and yields polymers which contain carboxyl end groups. The aromatic dicarboxylic acid dichlorides prepared by this method are dark in colour due to the presence of impurities and contain troublesome carbamic acid chlorides formed by reaction with the catalysts (see Chem. Ref. 1973, Vol.73, No.1, page 77 or Angewandte Chemie (1974), Year 1962, No. 21, page 864).

If colourless dicarboxylic acid dichlorides are to be obtained, the crude products must be purified by recrystallisation or distillation. This requires additional effort and expense and reduces the yield. In the case of aromatic dicarboxylic acid dichlorides there is also the risk of spontaneous decomposition.

The present invention relates to a process for the preparation of pure aromatic dicarboxylic acid dichlorides in one stage by reacting an aromatic dicarboxylic acid with phosgen in the presence of an N-alkyl-piperidine or an N-alkylmorpholine, the alkyl containing 1 to 6 carbon atoms.

The aromatic dicarboxylic acid dichlorides obtained are virtually colorless and contain 0.1% or less of impurities so that they can be used without further purification for the preparation of colorless high molecular weight polycondensates.

The cyclic aza-compounds used as catalysts according to the present invention can be removed almost completely by partial distillation of the reaction mixture. Residues of catalysts do not interfere with the conversion of the aromatic dicarboxylic acid dichlorides into high molecular weight polycondensates.

Suitable catalysts for the purposes of the present invention are N-alkyl-pyrrolidines, -piperidines or -morpholines having 1 to 6 carbon atoms in the alkyl group.

$C_1$–$C_6$ alkyl is preferably methyl, ethyl, propyl, isopropyl, butyl, sec.-butyl and tert.-butyl, as well as N-phenyl and N-hexyl. The following are particularly suitable catalysts: N-ethylpyrrolidine, N-ethylpiperidine, N-ethylmorpholine, N-isopropylpyrrolidine, N-isopropylpiperidine and N-isopropylmorpholine.

The catalysts are generally used in quantities of from 0.2 to 3%, by weight, preferably from 0.5 to 1.5% by weight, based on the aromatic dicarboxylic acids used. The preferred aromatic dicarboxylic acids correspond to the following general formulae:

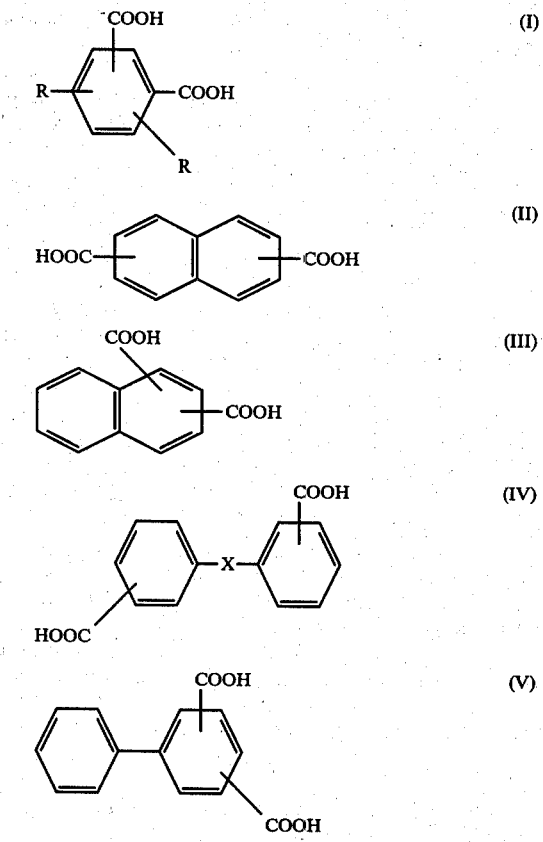

wherein R represents H, $C_1$–$C_4$ alkyl or halogen (preferably chlorine or bromines); and X represents a single bond,

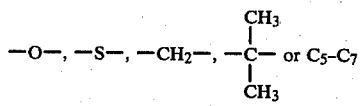

cycloalkylene.

Mixtures may also be used.

The following are mentioned as examples: phthalic acid, isophthalic acid, terephthalic acid, mixtures of isophthalic and terephthalic acids, diphenic acid and 1,4-napthalene dicarboxylic acid.

The solvent or diluent used is preferably the aromatic dicarboxylic acid dichloride or mixture of dicarboxylic acid dichlorides formed during the reaction. Inert diluents, such as aliphatic or aromatic hydrocarbons, halogen-substituted aromatic hydrocarbons, halogen-substituted aliphatic hydrocarbons or saturated aliphatic ethers, may also be added. The reaction temperature is generally from 110° to 180° C., preferably from 140° to 160° C.

The molar ratio of aromatic dicarboxylic acid to phosgene is preferably from 1:2 to 1:2.5, i.e. it is advisable to use a slight excess of phosgene to replace the losses which occur as gaseous $CO_2$ and HCl are expelled from the reaction mixture during phosgenation.

The process according to the present invention may be carried out batchwise or continuously. In a continuous embodiment, a solution of aromatic dicarboxylic acid, dicarboxylic acid dichloride and catalyst are passed downwards through a reaction tube against an upward stream of gaseous phosgene, while aromatic dicarboxylic acid dichloride and catalyst are removed from the bottom of the reaction tube.

In batch-wise embodiment, aromatic dicarboxylic acid, aromatic dicarboxylic acid dichloride and catalyst are introduced into a reaction vessel at normal pressure. The reaction mixture is then heated to from 140° to 160° C., with stirring. The aromatic dicarboxylic acid partially or completely goes into solution under these conditions. From 2 to 2.5 mol of gaseous phosgene per mol of aromatic dicarboxylic acid are introduced at this temperature.

After the removal of excess phosgene and gaseous HCl and $CO_2$ and part or all of the catalyst by brief application of a vacuum, a residue containing 99.9% or more of aromatic dicarboxylic acid dichlorides is obtained. This may be converted into high molecular weight, colourless polycondensates without further purification.

EXAMPLE 1

203 g (1 mol) of isophthalic acid dichloride, 166 g of isophthalic acid (1 mol) and 2.5 ml (2.06 g) of N-ethyl piperidine are heated to 149° C. in a round-bottomed flask equipped with a thermometer and stirrer and a deep freeze condenser which is maintained at −20° C. with cooling brine. Phosgene (ca. 240 g) continues to be introduced, with stirring at from 149° to 158° C. until the temperature in the reaction mixture falls (to ca. 145° C.). Any further phosgene introduced boils under reflux.

When the reaction mixture has cooled to 120° C., a water jet vacuum is applied to remove excess phosgene, any gaseous HCl and $CO_2$ dissolved in the reaction mixture and the major proportions of catalyst.

406 g of an almost colourless residue of isophthalic acid dichloride which is 99.9% pure (determined titrimetrically) are obtained. COOH: <0.07%.

EXAMPLE 2

101.5 g (0.5 mol) of isophthalic acid dichloride, 101.5 g (0.5 mol) of terephthalic acid dichloride, 83 g (0.5 mol) of isophthalic acid, 83 g (0.5 mol) of terephthalic acid and 2.5 ml (2.06 g) of N-ethylpiperidine are reacted with phosgene as described in Example 1.

405.5 g of an almost colourless residue consisting of a mixture of isophthalic and terephthalic acid dichloride which is 99.88% pure are obtained.

EXAMPLE 3

Method as in Example 2, but using 1.25 ml (1.03 g) of N-ethylpiperidine (=half the quantity of catalyst used in Example 2). Phosgenation time: 7 hours. Yield: 405 g of an almost colourless mixture of isophthalic and terephthalic acid dichlorides which is 99.94% pure. N: 49–54 ppm=0.05% N-ethylpiperidine COOH: <0.02%.

EXAMPLE 4

203 g (1 mol) of isophthalic acid dichloride, 203 g (1 mol) of terephthaic acid dichloride, 166 g of isophthalic acid (1 mol), 166 g (1 mol) of terephthalic acid and 2.5 ml (2.06 g) of N-ethylpiperidine are phosgenated with 470 g of phosgene as indicated in Example 1. When all the phosgene has been introduced, 166 g (1 mol) of isophthalic acid and 166 g (1 mol) of terephthalic acid are added and phosgenation is continued using a further 460 g of phosgene at from 146° to 154° C. and completed within ca. 10 hours without additional catalyst.

After application of a water jet vacuum at 120° C. and removal of the volatile constituents, 1216 g of an almost colourless mixture of isophthalic and terephthalic acid dichlorides are obtained having a degree of purity of 99.9%.

EXAMPLE 5

Method as in Example 2, but using 2.06 g of N-isopropyl morpholine as catalyst. Yield: 405 g of an almost colourless mixture of isophthalic and terephthalic acid dichlorides having a degree of purity of 99.9%.

EXAMPLE 6

Method as in Example 2, but using 2.06 g of N-ethylpyrrolidine as catalyst. Yield: 406 g of an almost colourless mixture of isophthalic and terephthalic acid dichlorides having a degree of purity of 99.88%.

We claim:

1. A process for preparing an aromatic dicarboxylic acid dichloride which comprises reacting at least one aromatic dicarboxylic acid selected from the group consisting of isophthalic acid and terephthalic acid in one stage with phosgene in the presence of a solvent or diluent and at a temperature of 110° to 180° C. in the presence of 0.2 to 3% by weight, based on said aromatic dicarboxylic acid, of an N-alkylpiperidine, N-alkyl-pyrrolidine or N-alkyl-morpholine, each said alkyl moiety having 1 to 6 carbon atoms.

2. The process of claim 1 wherein said solvent or diluent is the aromatic dicarboxylic acid dichloride formed during the reaction, a mixture of aromatic dicarboxylic acid dichlorides formed during the reaction, an aliphatic or aromatic hydrocarbon, a halogen substituted aliphatic hydrocarbon or a saturated aliphatic ether.

* * * * *